United States Patent [19]

Braid et al.

[11] Patent Number: 4,536,192
[45] Date of Patent: Aug. 20, 1985

[54] ADDITIVES FOR IMPROVING THE RESEARCH OCTANE NUMBER OF LIQUID HYDROCARBON FUELS

[75] Inventors: Milton Braid, Westmont; Phillip S. Landis, Woodbury, both of N.J.

[73] Assignee: Mobil Oil Corporation, New York, N.Y.

[21] Appl. No.: 899,682

[22] Filed: Apr. 24, 1978

[51] Int. Cl.³ ............................................. C10L 1/30
[52] U.S. Cl. ...................................................... 44/68
[58] Field of Search .................... 44/68; 252/42.7; 260/45.75 M, 439 R

[56] References Cited

U.S. PATENT DOCUMENTS

| 2,380,299 | 7/1945 | Evans et al. | 260/429 D |
| 2,409,687 | 10/1946 | Rogers et al. | 252/42.7 |
| 3,390,160 | 6/1968 | Heller et al. | 260/429 D |
| 4,090,970 | 5/1978 | Braid | 44/68 |
| 4,119,548 | 10/1978 | Braid | 44/68 |
| 4,151,100 | 4/1979 | Braid | 260/439 R |

Primary Examiner—Y. Harris-Smith
Attorney, Agent, or Firm—Alexander J. McKillop; Michael G. Gilman; Howard M. Flournoy

[57] ABSTRACT

Transition metal complexes of thiobis(alkylphenols) provide an increase in the research octane number of fuels suitable for use in internal combustion engines.

2 Claims, 1 Drawing Figure

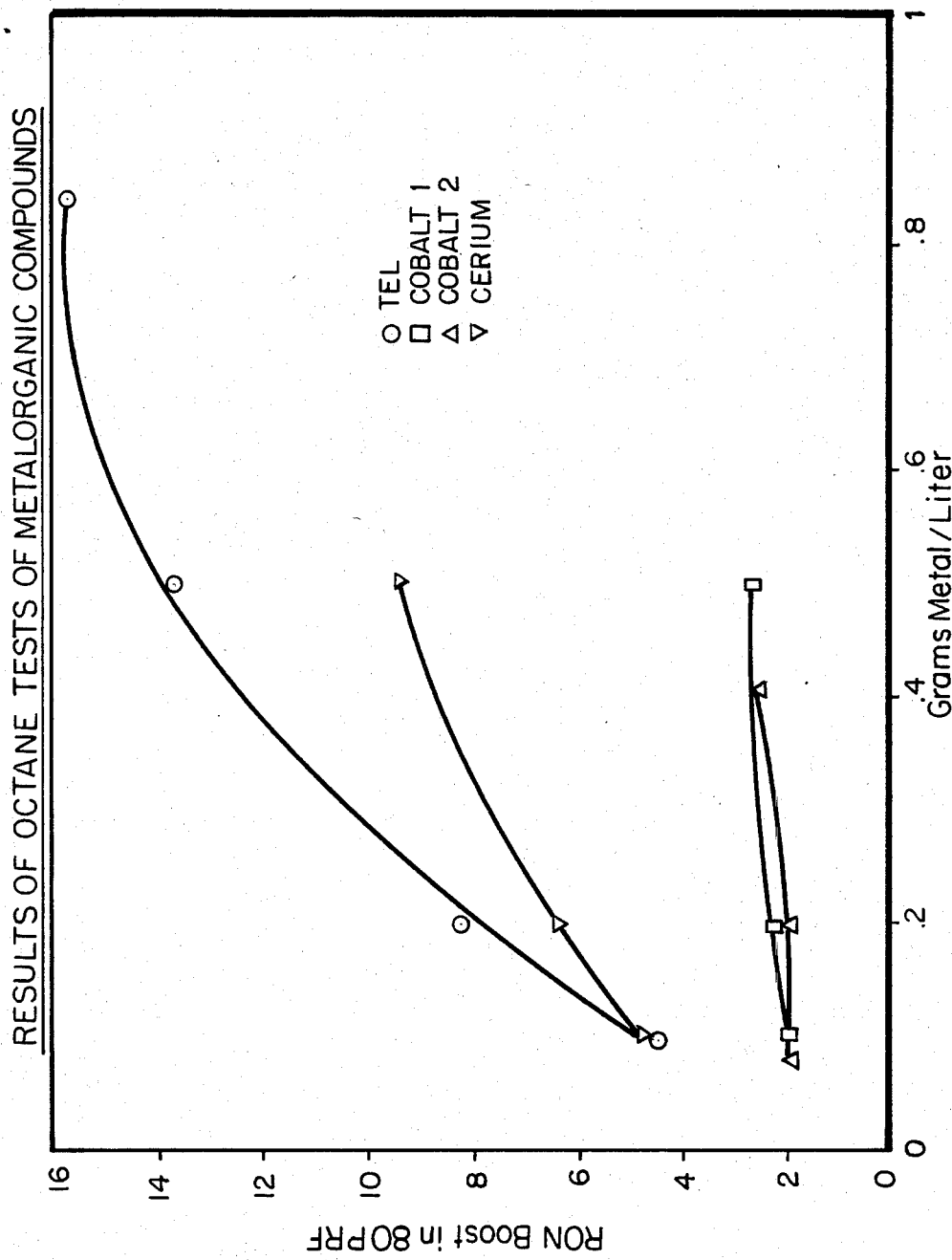

ADDITIVES FOR IMPROVING THE RESEARCH OCTANE NUMBER OF LIQUID HYDROCARBON FUELS

BACKGROUND OF THE INVENTION

1. Field of the Invention

This invention relates to transition metal thiobis (alkylphenolates) and thiobis(alkylphenol-phenolates) as novel means for increasing the research octane number of liquid hydrocarbon fuels and to organic compositions thereof containing a minor amount of said organosulfur-containing compounds and a major amount of said hydrocarbon fuel.

A more particular aspect this invention is directed to compositions comprising said organosulfur-containing compounds and liquid hydrocarbon fuels suitable for use in internal combustion engines. The subject thiobis-(alkylphenolates) and thiobis(alkylphenol-phenolates), when complexed with certain alkylamines, arylamines and hydroxy compounds also function to increase the octane rating of hydrocarbon base fuels.

2. Description of the Prior Art

In British Patent Specification No. 1,263,910 (1972), there is disclosed bis(stilbenedithiolato)nickel as an antioxidant for plastic materials, the compound also being useful in lube oils and functional fluids. Further, U.S. Pat. Nos. 2,703,786, 2,716,090, and 3,210,277 discloses the use of polyvalent metal (e.g. Ni) salts of alkyl phenol sulfides as oxidation inhibitors and plasticizing agents. Various polyvalent metal (e.g. nickel) compounds are disclosed in the patent literature, for example, U.S. Pat. No. 3,630,897 discloses metal salts (e.g. nickel, iron, zinc) of substituted dithiocarbamic acids and U.S. Pat. No. 3,252,910 discloses compounds such as nickel N,N-substituted dithiooxamides. U.S. Pat. Nos. 2,971,940 and 2,971,941 disclose nickel phenol-phenolate complexes as being useful in stabilizing polyethylene and polypropylene.

None of the foregoing disclosures, however, show liquid organic e.g., hydrocarbon base fuel compositions such as gasolines containing the organosulfur-containing compound and complexes described in accordance with this invention.

SUMMARY OF THE INVENTION

This application is directed to the discovery that the below described organosulfur-containing transition metal complexes provide improved research octane number rating for liquid hydrocarbon fuels when they are added to said fuels in minor effective amounts. So-called coordination compounds of these complexes with certain alkylamines, arylamines, phenols or alcohols are also highly effective for increasing the octane number rating of liquid hydrocarbon fuels.

The organic sulfur-containing compounds in accordance with the present invention include thiobis(alkylphenolates) and thiobis(alkylphenol-phenolates) having the following structures:

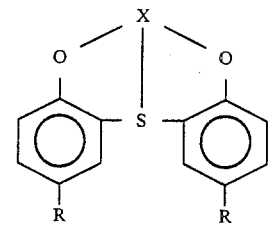

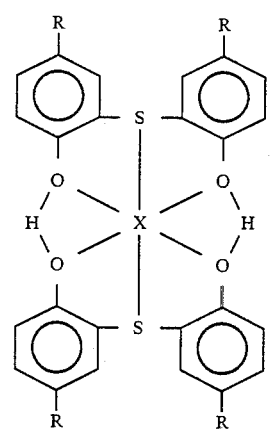

in which R is either hydrogen or an alkyl group having from 1 to about 30 carbon atoms preferably 1–16 or 4–8 carbon atoms in any isomeric arrangement and X is a transition metal selected from copper, cobalt, iron and nickel.

The thiobis(alkylphenol-phenolates) in accordance herewith may also be structurally represented as follows:

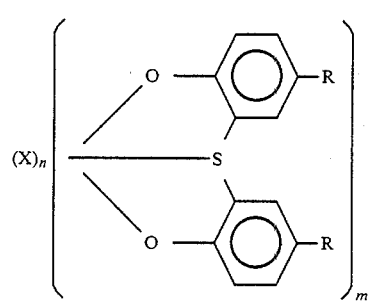

where R and X are as described hereinabove, n=1 or 2 and m=1 to 3.

Representative of hydroxy derivatives, i.e., alcohols or phenols, are coordination compounds of the aforementioned.

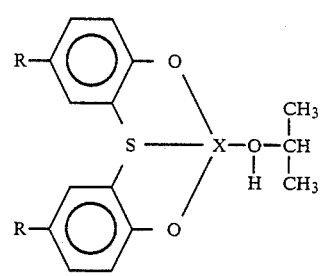

where R and X are as previously described.

Representative of the amine derivatives are e.g., n-butylamines.

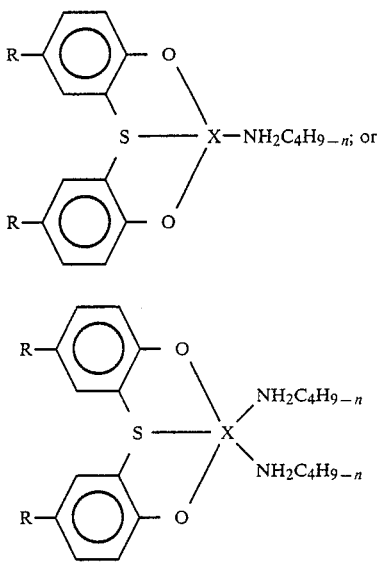

where R and X are as previously described.

BRIEF DESCRIPTION OF THE DRAWING

The drawing is a plot of the effectiveness in increasing RON (Research Octane Number) of a transition metal organosulfur-containing complex in accordance with the invention compared at low metal concentration with that of other organometallic compounds.

DESCRIPTION OF SPECIFIC EMBODIMENTS

The above described transition metal complexes and coordination compounds thereof may be prepared in any convenient manner known in the art. More specifically: nickel thiobis(4-t-octylphenol-phenolate) is a commercial product and may be conveniently prepared in accordance with U.S. Pat. No. 2,971,940. Nickel thiobis(4-t-octylphenolate) may also be obtained commercially or conveniently prepared in accordance with U.S. Pat. No. 2,971,941.

The organosulfur containing complexes of cobalt, copper and iron may be prepared in similar manner. Cobalt thiobis (alkylphenolates) and cobalt thiobis (alkylphenol-phenolates) may also be prepared in accordance with copending U.S. applications Ser. Nos. 847,461 filed Oct. 31, 1977 and 853,353 filed Nov. 21, 1977, now U.S. Pat. No. 4,151,100.

With respect to the coordination compounds, nickel thiobis (alkylphenolate) complex with n-butylamine is a commercially available product which may be conveniently prepared in accordance with Example 8 of U.S. Pat. No. 3,215,717.

The n-butylamine coordination compounds of cobalt, copper and iron may be prepared in similar manner. However, the coordination compounds of cobalt and n-butylamine may be prepared as described in the aforementioned copending U.S. application Ser. No. 853,353, now U.S. Pat. No. 4,151,100.

The hydroxy coordination compounds are generally prepared by reacting, under appropriate conditions, the transition metal complex, e.g., cobalt thiobis (alkylphenolate) or cobalt thiobis (alkylphenol-phenolates) with an hydroxy compound such as phenol or propanol. For example in preparing [2,2'-thiobis-(4-t-octylphenolato)]-2-propanol cobalt, 2,2'-thiobis-(4-t-octylphenol) is reacted with cobalt II acetate tetrahydrate with heat in a suitable solvent. The resulting complex is recovered from the filtrate upon distillation of the solvent and then reacted with 2-propanol. Additionally, for more specific details of such preparations please refer to the above mentioned copending applications, Ser. Nos. 847,461 and 853,353. Any of the transition metal coordination compounds described herein may be prepared, as described in copending U.S. patent application No. 853,353.

Especially preferred of the above-described complexes and coordination compounds thereof are those wherein the alkyl groups are 4-t-octyl or 1,1,3,3-tetramethyl-butyl.

The amines suitable for use in preparing the above-referred to amine complexes or coordination compounds of the transition metal thiobis(alkylphenolates) and thiobis(alkylphenol-phenolates) may be alkyl or aryl. Suitable alkyl amines include $C_1$–$C_{30}$ alkyl amines such as methylamine, n-butylamine, dimethylbutylamine, hexylamine and the like.

The arylamines suitable for use herein are preferably selected from the following non-exhaustive list: aniline, toluidine, tolidine, anisidine, butyl aniline, dodecylaniline and similar substituted anilines, benzylamine and alkylated benzylamines. Hexyl aniline and butylaniline are preferred. However, it is understood that this is a non-limitinng list—any alkyl or arylamine appropriate in view of those disclosed above may be used.

Alcohols suitable for use in preparing the hydroxy legend containing compounds referred to hereinabove are of the general formula ROH where R is an alkyl or substituted alkyl group. The alcohol may be primary or secondary. Preferred are lower alkyl alcohols such as methanol, ethanol, propanol, 2-propanol and n-butanol and 2-butanol. Phenols suitable for use in herein include phenol cresol, t-octyl phenol, p-methoxyphenol and the like. Phenol is preferred, although any phenol appropriate in view of those disclosed above may be used.

The organosulfur-containing complexes in accordance with the invention are employed in a minor effective amount thereby increasing the octane rating of the fuel to which they are added. In many instances, the complexes are effectively employed in an amount from about 0.01 to about 0.25 gram of metal per liter of fuel and preferably from about 0.05 to about 0.2 grams of metal per liter of fuel. As hereinbefore indicated, the organic sulfur-containing transition metal complexes and coordination compounds thereof may be incorporated into any liquid hydrocarbon combustion fuel especially liquid hydrocarbon fuel suitable for use in internal combustion engines.

The liquid hydrocarbon base fuels contemplated for use herein are generally distillate fuels having a distillation range between about 100° F. and about 750° F. The distillation range of each individual fuel will cover a narrower boiling range falling, nevertheless, within the above-specified limits, each will boil substantially continuously throughout its distillation range. Gasolines, diesel fuels, gas turbine fuels and the like are included.

The gasolines that are improved by the additive compositions of this invention, are mixtures of hydrocarbons having an initial boiling point falling between about 75° F. and about 135° F. and an end-boiling point falling between about 250° F. and about 450° F. As is well known in the art, motor gasoline can be straight run gasoline or, as is more usual, it can be a blend of two or more cuts of materials including straight run stock, catalytic or thermal reformate, cracked stock, alkylated natural gasoline, and aromatic hydrocarbons.

The following examples are merely exemplary and are not meant to limit the invention in any way.

EXAMPLE 1

The primary reference fuel (PRF) was standard 80 octane liquid hydrocarbon fuel normally used in internal combustion engines having an initial bp of at least 75° F. and an end point bp of no greater than about 450° F.

EXAMPLE 2

NiTBP, nickel 2,2'-thiobis-(4-t-octylphenolate) may be obtained commercially. Its method of preparation is as described in the aforementioned U.S. Pat. No. 2,971,941.

EXAMPLE 3

NiTBP.NH$_2$C$_4$H$_9$-n; [2,2'-thiobis-(4-t-octylphenolato)]-n-butylamine nickel II was obtained commercially. Its method of preparation is as described in U.S. Pat. No. 3,215,717.

EXAMPLE 4

NiTBP.i-C$_3$H$_7$OH; [2,2'-thiobis-(4-t-octylphenolato)]-2-propanol nickel II was prepared as follows:

One hundred fifty grams of nickel 2,2'-thiobis-(4-t-octylphenolphenolate) (purchased commercially and manufactured in accordance with U.S. Pat. No. 2,971,940), melting range of 147°-149° C., was added to about 650 ml. of 2-propanol. The mixture was then heated while stirring. As the reaction temperature approached 85° C. all of the solids dissolved. After refluxing for about ¼ to ½ hr. solids again began to precipitate. The reaction mixture became progressively more turbid and after 1.5 hr. of refluxing the hot mixture was filtered and the solids collected and dried. 75.7 g. of a light green colored solid with a melting point higher than 300° C. were obtained. Elemental analysis of solids prepared in this way corresponded to the nickel 2,2'-thiobis-(4-t-octylphenolate) complex with 2-propanol [2,2'-thiobis-(4-t-octylphenolate)]-2-propanol nickel II.

Anal. Calcd for C$_{31}$H$_{48}$O$_3$S Ni: C, 66.6; H, 8.7; S, 5.7 Ni, 10.49 Found: C, 65.0; H, 8.5; S, 5.8; Ni, 10.52.

EXAMPLE 5

Co$_2$(TBP)$_3$; dicobalt [2,2'-thiobis-(4-t-octylphenolate)]$_3$ was prepared in accordance with copending U.S. application Ser. No. 847,461 filed Oct. 31, 1977.

EXAMPLE 6

Co TBP.i-C$_3$H$_7$OH; [2,2'-thiobis-(4-t-octylphenolate)]-2-propanol cobalt II was prepared in accordance with copending U.S. Pat. application No. 853,353 filed Nov. 21, 1977.

EXAMPLE 7

Fe (TBP)$_2$; iron 2,2'-thiobis-(4-t-octylphenolphenolate) was prepared in the following manner:

To a solution of 2,2'-thiobis-(4-t-octylphenol) (88.4 g) in xylene (300 ml) heated almost to reflux temperature (about 130° C.) there was added while stirring under a nitrogen atmosphere anhydrous iron II acetate (17.39 g.). The temperature was raised and an azeotropic mixture of xylene and acetic acid was removed by distillation while fresh xylene was concurrently added to maintain approximately constant volume of the reaction mixture. This process was continued for several hours until no further trace of acetic acid could be detected. The reaction mixture was freed of solvent by rotary evaporation and the residue was extracted with pentane. The extract was then filtered to remove any unreacted thiobisphenol and inorganics. Removal of the solvent pentane from the filtrate left the iron 2,2'-thiobis-(4-t-octylphenol-phenolate) as a dark purple friable solid, m.p. 90°-93° C.

Anal. Calc'd for C$_{56}$H$_{82}$O$_4$S$_2$Fe: C, 71.61; H, 8.80 S, 6.83; Fe, 5.95. Found: C, 72.02; H, 8.90; S, 6.46; Fe, 5.86.

The effectiveness of Examples 2-7 in increasing the research octane number (RON) of the primary reference fuel (PRF) was determined and thereafter recorded in Table 1.

The figure is a plot of the effectiveness of cobalt compounds in accordance with the invention compared at low metal concentration with that of tetraethyl lead (TEL). At about 0.1 g of metal/liter, the cobalt compounds (cobalt 1 was Ex. 5 and cobalt 2 was Ex. 6) are nearly half as effective as TEL. The cobalt compounds increased the research octane number (RON) of the primary reference fuel (PRF) 2 octane numbers, the TEL increased it 4+ octane numbers. Also compared was a cerium compound [tetrakis(2,2,6,6-tetramethyl-3,5-heptane dionato) cerium], H(thd)Ce which at 0.1 g metal concentration was about effective as the TEL.

The data tabulated in the Table and the graph clearly demonstrate the utility of this invention in liquid hydrocarbon fuels.

While this invention has been described with reference to preferred compositions and components therefore, it will be understood by those skilled in the art that departure from the preferred embodiments can be effectively made and are within the scope of the specification.

TABLE 1

| NUMBER (RON) IMPROVEMENT 1 g. of Additive/Liter of Fuel | | | | |
| --- | --- | --- | --- | --- |
| Additive | Metal | Conc. g. Metal/ Liter | RON | ΔRON |
| None | — | — | 80 | 0 |
| Example 1 (PRF) | | | | |
| Example 2 Ni TBP | Ni | 0.118 | 80.8 | 0.8 |
| Example 3 Ni TBP.NH$_2$C$_4$H$_9$—n | Ni | 0.103 | 80.9 | 0.9 |
| Example 4 Ni TBP.i-C$_3$H$_7$OH | Ni | 0.105 | 80.9 | 0.9 |
| Example 5 Co$_2$ (TBP)$_3$ | Co | 0.082 | 82.0 | 2.0 |
| Example 6 Co TBP.i-C$_3$H$_7$OH | Co | 0.105 | 82.0 | 2.0 |
| Example 7 Fe (TBP)$_2$ | Fe | 0.06 | 80.4 | 0.4 |

In the attached plot the effectiveness of the cobalt compounds may be compared at low metal concentration with that of tetraethyl lead (TEL). At about 0.1 g. of metal/liter the cobalt compounds (2 octane numbers) are nearly half as effective as TEL (4+ octane numbers).

What is claimed is:

1. A method of increasing the octane research number of liquid hydrocarbon fuels, selected from hydrocarbon fractions having an initial boiling point of at least about 75° F., and boiling substantially continuously throughout their distillation range, suitable for use in internal combustion engines comprising intimately admixing with said hydrocarbon base fuel an organosulfur-containing metal compound selected from a minor effective amount of a cobalt thiobis ($C_1$–$C_{30}$ alkylphenate having the following general structure
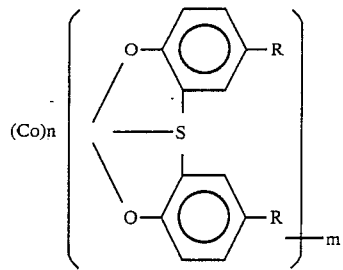
where R is an alkyl group of from about 4 to 16 carbon atoms, m is 3 and n is 2.
2. The method of claim 1 where R is a 4-t-octyl group.
* * * * *